Figure 1:
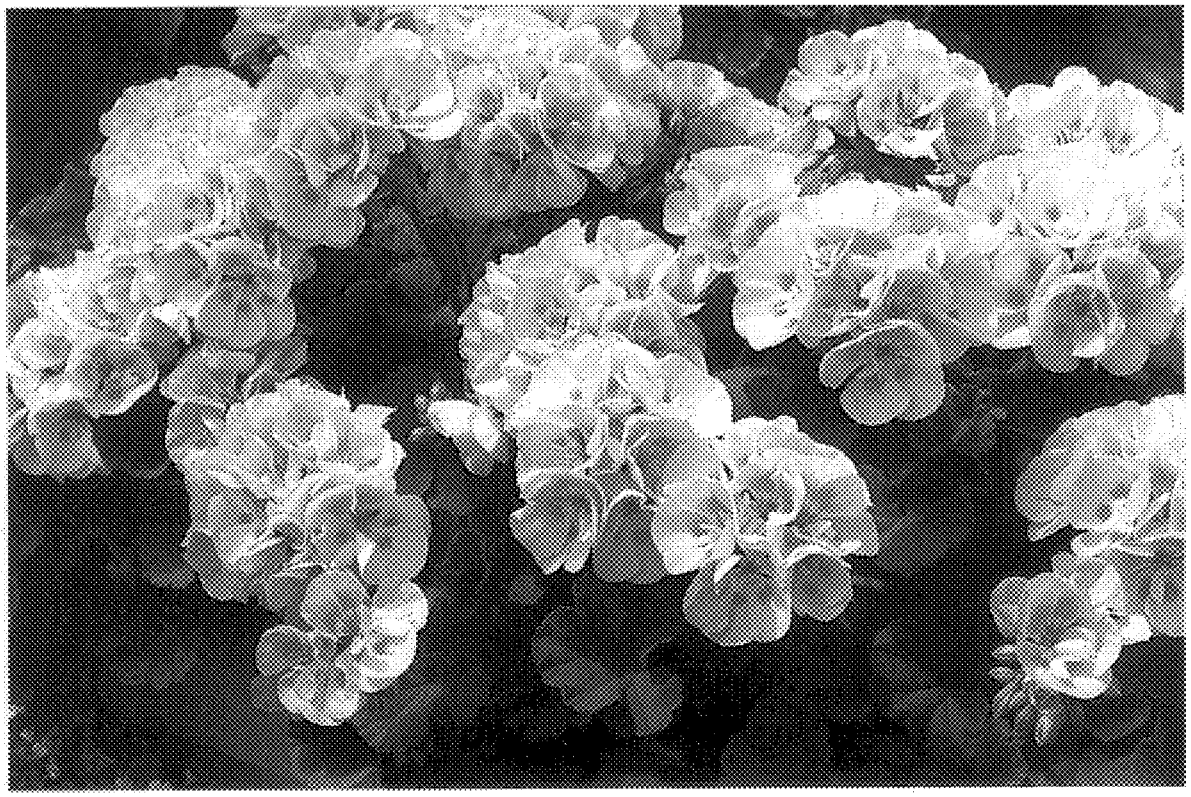

US00PP10971P

United States Patent [19]

Hanes

[11] Patent Number: Plant 10,971

[45] Date of Patent: Jun. 22, 1999

[54] GERANIUM PLANT NAMED 'AMRI LIGHT PINK SPLA'

[75] Inventor: Mitchell Eugene Hanes, Morgan Hill, Calif.

[73] Assignee: Goldsmith Seeds, Inc., Gilroy, Calif.

[21] Appl. No.: 08/962,972

[22] Filed: Nov. 6, 1997

[51] Int. Cl.[6] ..... A01H 5/00

[52] U.S. Cl. ..... Plt./325

[58] Field of Search ..... Plt./87.12, 325, Plt./328, 329

[56] References Cited

U.S. PATENT DOCUMENTS

P.P. 9,152 5/1995 Enthoven ..... Plt./87.12

OTHER PUBLICATIONS

UPOV–ROM, Jan. 1998, Plant Variety Database, GTI Jouve Retrieval Software, citation for 'Amri Light Pink Spla'.

*Primary Examiner*—Howard J. Locker

*Attorney, Agent, or Firm*—Rothwell, Figg, Ernst & Kurz

[57] ABSTRACT

A new geranium cultivar particularly distinguished by free flowering plant with a mound shaped plant habit, green foliage without zonation, semi-double flowers that are light pink with a rose red spot.

1 Drawing Sheet

BACKGROUND OF THE NEW PLANT

The present invention comprises a new and distinct cultivar of geranium, botanically known as *Pelargonium hortorum* Bailey, and hereinafter referred to by the cultivar name Amri Light Pink Spla. The new cultivar is propagated from a seedling resulting from the cross of seed parent Melody (U.S. Plant Pat. No. 8,006) which has a bi-colored pink semi-double flower and the pollen parent 4134-1 (a non-patented breeding line which has a bi-colored light lavender semi-double flower).

Amri Light Pink Spla is a product of a planned breeding program intended to create new geranium cultivars with bicolored light pink with rose red spot patterns, flowers that are semi-double flower form, and a plant with green foliage.

The new cultivar was created in 1995 in Gilroy, Calif. and has been repeatedly asexually reproduced by cuttings in Gilroy, Calif. and Guatemala over a two year period. It has also been trialed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit including the bloom.

DESCRIPTION OF THE NEW CULTIVAR

The following detailed descriptions set forth the distinctive characteristics of Amri Light Pink Spla. The data which defines these characteristics were collected from asexual reproductions carried out by Goldsmith Seeds, Inc. in Gilroy, Calif. The plant history was taken on 11 week old plants, blossomed under natural light in a greenhouse and color readings were taken in the greenhouse in Gilroy, Calif. on Mar. 25, 1997 between 1–4 p.m. under ambient light. Color references are to The R.H.S. Colour Chart of The Royal Horticultural Society of London (R.H.S.).

The Plant

Classification:

*Botanical.*—*Pelargonium hortorum* Bailey.

*Commercial.*—Zonal geranium.

Height: 10 to 12 cm, as a 4 inch pot plant, excluding blooms.

Growth: Upright branches with a mounded plant habit.

Finishing time: Finishing time of a 4-inch pot from a rooted cutting is 10 weeks.

Foliage: Abundant quantity, no zonation.

Leaves:

*Size.*—Diameter about 5.7 cm.

*Shape.*—Rounded cordate with occasional up folding between veins.

*Margin.*—Irregularly crenate.

*Texture.*—Leathery and pubescent on both surfaces, especially along veins.

*Ribs and veins.*—Distinctly palmate, 2.8 to 3.3 cm long.

*Color.*—Upper side: Green 147B R.H.S. Under side: Lighter green 146B R.H.S. color. Ribs and veins not prominently different from upper surface.

*Petioles.*—About 2.9 to 3.2 cm in length, green 146C R.H.S.

The Bud

Size:

*Diameter.*—About 8 mm.

*Length.*—About 2.4 cm at time of bud opening.

Shape: Pointed ovoid.

Color: Petals when sepals first divide, pink 55C–D R.H.S.

Sepals: 5 in number, flat behind petals. Pointed linear lanceolate, green R.H.S. 143B in an open flower.

The Flower

Blooming habit: Continuous throughout the year.

Size: Approximately 4.7 cm in diameter, 1.5 cm deep, irregularly radially symmetrical.

Form: Cup-shaped when bloom first opens, later flattening to shallow cup shape with maturity.

Petals: 5–6 imbricate outer petals, 2.1–2.3 cm wide and approximately 2.5 cm long. Several inner smaller petaloids of varying shape. Both the outer petals and inner petaloids are light pink 73C R.H.S. The outer petals have a rose red spot pattern, 66B R.H.S. in the central region. The upper two petals have a feathered vein pattern, rose red 66B R.H.S., up to the central spot. The veins are also 66B R.H.S. Color changing little with age. Underside of petals are blush white 73D R.H.S. Petals and petaloids soft and satiny.

Pedicel: Approximately 2.1–2.5 cm in length.

Persistence: Non-shattering flower.

Inflorescence

Type: An umbel approximately 13 cm over the leaves, having a diameter of 12 cm and depth of 9 cm, composed of approximately 25 flowers, erect or laterally ascending.

Peduncle: Approximately 7.5–12 cm in length, mostly 10.5 cm, green 146B R.H.S. in color.

Reproductive Organs

Stamens:

*Anthers.*—5–7 positioned below the mature stigma, dull red prior to anthesis.

*Filaments.*—Primarily white with red at the point of the anther attachment.

*Pollen.*—Orange in color.

Pistil:

*Number.*—1

*Length.*—Approximately 7 mm.

*Stigma.*—5 linear lobes of near equal length, curling back toward ovary, purplish-red in color.

*Style.*—Length: About 2 mm. Color: Pink.

*Ovaries.*—At anthesis, densely pubescent with white hairs, oblong. Green drying to a light brown at maturity.

*Fruit.*—Will set some seed.

I claim:

1. A new and distinct cultivar of geranium plant substantially as herein shown and described, named Amri Light Pink Spla, that is characterized by: free flowering plant with a mound shaped plant habit, green foliage without zonation, semi-double flowers that are light pink with a rose red spot.

* * * * *